United States Patent [19]

Reid et al.

[11] 4,137,267

[45] Jan. 30, 1979

[54] CATALYTIC HYDROGENATION PROCESS

[75] Inventors: Robert E. Reid, Houston, Tex.; Hyung K. Zang, Hopewell Junction, N.Y.

[73] Assignee: Texaco Inc., New York, N.Y.

[21] Appl. No.: 770,339

[22] Filed: Feb. 22, 1977

[51] Int. Cl.$^2$ .................. C07C 85/00; C07B 29/00
[52] U.S. Cl. ..................... 260/583 P; 260/583 N; 260/690; 260/700
[58] Field of Search ............. 260/583 K, 700, 583 P

[56] References Cited

U.S. PATENT DOCUMENTS

| 1,873,876 | 8/1932 | Downs | 260/700 |
|---|---|---|---|
| 1,916,473 | 7/1933 | Forrest et al. | 260/700 |
| 1,955,873 | 4/1934 | Deanesly | 260/700 X |
| 2,373,501 | 4/1945 | Peterson et al. | 260/700 X |
| 3,346,640 | 10/1967 | Guyer et al. | 260/583 R |
| 3,372,195 | 3/1968 | Little | 260/570.7 |
| 3,632,625 | 1/1972 | Funten et al. | 260/583 K X |
| 4,003,933 | 1/1977 | Drake | 260/583 K |

Primary Examiner—Winston A. Douglas
Assistant Examiner—John Doll
Attorney, Agent, or Firm—Thomas H. Whaley; Carl G. Ries; George J. Darsa

[57] ABSTRACT

A catalytic hydrogenation process for preparing alkyl-1,3-diaminopropanes by contacting an alkyl aminopropionitrile in the liquid phase with hydrogen and ammonia in the presence of a non-reactive organic solvent and a hydrogenation catalyst, the process conducted at a rising reaction temperature ($\Delta T$) along with the progressive vaporization of the solvent.

14 Claims, No Drawings

CATALYTIC HYDROGENATION PROCESS

BACKGROUND OF THE INVENTION

This invention relates to a process for preparing alkyl diaminopropanes. More particularly, this invention relates to a process for the production of $C_{10}$ and higher alkyl-1,3-diaminopropanes from $C_{10}$ and higher alkyl aminopropionitriles.

In general, alkyl nitriles can be catalytically reduced to primary alkyl amines over a wide range of operating conditions. The process, however, produces as by-products significant amounts of secondary and tertiary amines. In an effort to improve the selectivity to primary amine products while reducing secondary and tertiary amine by-products, U.S. Pat. Nos. 2,160,578 and 2,165,515 describe procedures conducted under essentially isothermal conditions and in the presence of ammonia or low molecular weight amines. British Pat. No. 855,027 proposes that the formation of secondary and tertiary amines can be suppressed by carrying out the hydrogenation in the vapor phase using a hydrogenation catalyst in fluidized form. More recently, U.S. Pat. No. 3,163,676 discloses that improved results can be obtained by recycling the finished primary amine product to the hydrogenation zone thereby reducing the amount of secondary and tertiary amines formed.

With regard to the catalytic reduction of $C_{10}$ and higher alkyl aminopropionitriles to the corresponding alkyl diaminopropanes the reaction is exothermic in nature. Upon conducting the process in small or laboratory size reactors, the heat of reaction is easily dissipated through the reactor walls. Under such essentially isothermal conditions, the heat of reaction does not significantly affect the selectivity of the process. However, the heat of reaction is substantially retained in the liquid phase when larger or commercial size reactors are employed which in turn adversely affects the process selectivity. More particularly, we have found that the reaction is influenced by various equilibrium relationships wherein at lower temperatures partially reduced nitrile intermediate products react with formed primary amine product to produce undesirable secondary and tertiary amine by-products. At higher reaction temperatures, cracking of the molecule occurs wherein the alkyl aminopropionitriles are converted to lower molecular weight primary amines and propionitriles. While the reaction conditions, particularly the reaction temperature, can be controlled by external cooling means or through the use of various devices in the reaction zone, as by cooling coils, such means or devices can often times cause processing interruptions due to mechanical failures. A highly desirable process would be one capable of providing selective conversion of the nitrile to the alkyl diaminopropane, of being employed in a simple reactor design and with the ability of the process to self regulate the reaction temperature by the removal of heat from the liquid reactants in the reaction zone.

It is therefore an object of this invention to provide a process for the catalytic reduction of $C_{10}$ and higher alkyl aminopropionitriles to $C_{10}$ and higher alkyl-1,3-diaminopropanes.

Another object of this invention is to provide a process for selectively converting $C_{10}$ and higher alkyl aminopropionitriles to $C_{10}$ and higher alkyl-1,3-diaminopropanes.

Yet another object of this invention is to provide a process for the catalytic hydrogenation of $C_{10}$ and higher alkyl aminopropionitriles to $C_{10}$ and higher alkyl-1,3-diaminopropanes in high yields.

Yet another object of this invention is to provide a continuous catalytic hydrogenation process wherein $C_{10}$ and higher alkyl aminopropionitriles are reduced to $C_{10}$ and higher alkyl-1,3-diaminipropanes while simultaneously deterring the cracking to lower molecular weight primary amines and the formation of secondary and tertiary amines.

Other objects and advantages will become apparent from a reading of the following detailed description of the invention.

SUMMARY OF THE INVENTION

Broadly, this invention contemplates a process for preparing alkyl-1,3-diaminopropanes which comprises contacting an alkyl aminopropionitrile and an organic solvent in the liquid phase with hydrogen and ammonia in the presence of a hydrogenation catalyst at a reaction temperature of at least 180° F. and a pressure of at least 200 p.s.i.g. and maintaining the pressure sufficient to effect vaporization of said solvent at a rate limiting the rise in reaction temperature to between about 5 and 40° F. The contacting of the nitrile in the liquid phase is conducted at an increasing temperature ($\Delta T$), that is non-isothermally, and under conditions that permit progressive vaporization of the solvent in the course of the reaction. Vaporization of the solvent provides an effective self-regulating means of absorbing the heat of reaction thereby limiting the maximum reaction temperature in the liquid phase.

The process of our invention wherein alkyl aminopropionitriles are reduced to alkyl-1,3-diaminopropanes can be appreciated by referring to the following equation:

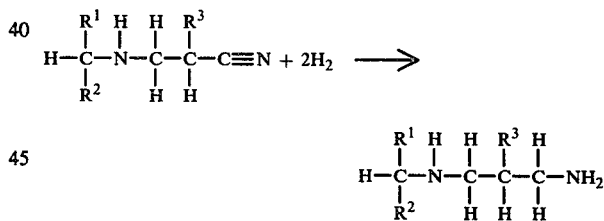

where $R^1$ is hydrogen or an alkyl group having from 1 to 12 carbon atoms, where $R^2$ is an alkyl group of from 9 to 24 carbon atoms, where the sum of $R^1$ and $R^2$ is from 9 to 29 carbon atoms and where $R^3$ is hydrogen or methyl. Preferred propionitrile starting materials contemplated herein are those where $R^1$ and $R^2$ are alkyl as described above. The propionitrile can be obtained by various methods as, for example, cyanoethylation of a $C_{10}$ to $C_{30}$ alkyl primary amine or mixtures of $C_{10}$ to $C_{30}$ primary amines with acrylonitrile or methylacrylonitrile in the presence of hydrogen chloride at temperatures of 160 to 170° F. The primary amine can be a primary alkyl primary amine or a secondary alkyl primary amine. In general, the propionitrile can be provided in yields as high as 95 percent or more by using a molar excess of primary amine to the acrylonitrile. The alkyl aminopropionitrile reactant employed in our process can be an individual nitrile or mixtures of nitriles. Moreover, the amine or mixtures of amines employed in preparing the propionitrile need not be separated from the nitrile and such mixtures are suitable feedstocks in the hydrogenation reaction. The mixtures can contain up to about 50 weight percent primary amine.

Illustrative of the nitriles employed as starting material in the instant invention, we mention 2-[n-decylaminol] propionitrile, 2-[secondary decyl primary amino] propionitrile, 1-methyl-2-[n-decylamino] propionitrile, 2-[n-undecylamino] propionitrile, 2-[secondary undecyl primary amino] propionitrile, 2-[n-dodecylamino] propionitrile, 1-methyl-2-[n-dodecylamino] propionitrile, 2-[n-tridecylamino] propionitrile, 2-[secondary tetradecyl primary amino] propionitrile, 2-[n-hexadecylamino] propionitrile, 2-[n-eicosylamino] propionitrile, 2-[n-tetracosylamino] propionitrile, 1-methyl-2-8 n-tetracosylamino] propionitrile and 2-[secondary tetracosyl primary amino] propionitrile. Mixtures of nitriles are also contemplated, as for example, mixtures of 2-[n-decylamino] propionitrile and 2-[secondary decyl primary amino] propionitrile; 2-[n($C_{10-14}$)alkylamino] propionitriles; 2-[secondary($C_{10-14}$) alkyl primary amino] propionitriles; 2-[n-tetradecylamino] propionitrile, 2-[n-pentadecylamino] propionitrile and 2-[n-hexadecylamino] propionitrile; 2-[secondary($C_{14-16}$) alkyl primary amino] propionitriles; 2-[secondary($C_{18-24}$) alkyl primary amino] propionitriles; 1-methyl-2-[secondary ($C_{10-14}$)alkyl primary amino] propionitriles; 1-methyl-2-[secondary($C_{14-16}$)alkyl primary amino] propionitriles; and 1-methyl-2-[secondary($C_{18-24}$)alkyl primary amino] propionitriles.

The reduction of the alkyl aminopropionitrile to the diaminopropane is conducted catalytically, that is, in the presence of a wide choice of conventional hydrogenation catalysts. Among the hydrogenation catalysts which can be selected we mention Group VIII metal catalysts where the metal can be platinum, palladium, rhodium, ruthenium, nickel or cobalt. A Group VII metal, such as rhenium, can also be present. The catalyst can be supported on conventional carrier materials, such as kieselguhr, alumina, silica, silica-alumina, carbon, pumice, porcelain, quartz and the like. Suitably, the catalyst is reduced prior to use at temperatures of, for example, 400 to 600° F. in a hydrogen environment thereby providing the Group VIII component in the metallic state. Metal oxide catalysts are unsuitable in the instant process in that essentially no reduction occurs in their presence. Preferred catalysts contemplated herein are nickel and palladium catalysts and particularly, a nickel on kieselguhr promoted with zirconium or palladium on carbon catalysts.

An important aspect of this invention relates to the use of a non-reactive organic solvent during the course of the nitrile reduction. The solvent or mixtures of solvents selected are those which are inert in the present reaction. In addition, the solvent must be capable of at least being partially vaporized in the course of the reaction and should preferably be capable of dissolving the starting nitrile and diaminopropane product. Solvents contemplated herein have normal boiling points of from about 85 to 175° F., preferably 85 to 150° F., and we employ weight ratios of solvent to nitrile of from about 2:1 to 20:1. The solvents are readily separated from the reaction product by, for example, distillation. Illustrative of the solvents we mention methanol, ethanol, ethylpropylether, methylacetate, ethylacetate, ethylformate, propylamine, diethylamine, 2,3-dimethylbutane and methylpentane and mixtures thereof. Cosolvents, such as pentane and butyl alcohol, can also be used wherein at least one of the materials, such as pentane, will vaporize to a substantial degree in the course of the reaction.

The contacting of the nitrile and solvent with the catalyst is undertaken in the presence of hydrogen and ammonia, where the volume of gaseous hydrogen and ammonia to liquid nitrile and solvent is at least 10:1 and up to about 100:1. In general, about 16 to 150 moles of hydrogen and 4 to 50 moles of ammonia are employed per mole of nitrile. Typically, the moles of hydrogen employed are in excess of the moles of ammonia employed. The processing parameters of temperature and pressure along with the amounts of hydrogen and ammonia provide conditions enabling substantial and progressive vaporization of the solvent. The hydrogen gas can be pure hydrogen or hydrogen in admixture with nitrogen, helium or light hydrocarbons, such as methane.

The catalytic hydrogenation is undertaken at a rising temperature within the range of about 180 to 260° F., preferably from about 200 to 240° F., and at pressures of from about 200 to 1,000 p.s.i.g. The process is conducted under a sufficient pressure to prevent the solvent from completely vaporizing prior to the completion of the hydrogenation reaction. The most appropriate pressure within the range set forth above can be determined after a selection of solvent has been made. Under the conditions described herein, the reaction is undertaken at a rising temperature ($\Delta T$). In batch reactions, the $\Delta T$ is apparent by a rise in temperature in the liquid phase. In continuous processes the $\Delta T$ can be ascertained by measuring the progressive rise in temperature through the catalyst bed. The increase in reaction temperature in the liquid phase is reflective of the heat of reaction and is controlled by the vaporization of the solvent such that the liquid phase will be permitted to undergo a rise in temperature ($\Delta T$) of at least 5° F. and up to about 40° F. The processing conditions described herein and particularly the pressure and rising reaction temperature enable increasing amounts of solvent to be vaporized in the reaction zone while the nitrile reactant remains in the liquid state. The presence of the solvent in the course of the exothermic catalytic reduction of the alkyl aminopropionitriles to alkyl-1,3-diaminopropanes effectively controls the hydrogenation reaction by removing heat of reaction from the liquid phase thereby limiting the maximum reaction temperature and deterring cleavage of the starting nitrile material to a primary amine and nitrile. In contrast, if a non-vaporizing solvent or a solvent having a higher boiling point than that herein contemplated is employed, a substantial portion of the heat of reaction will be retained in the liquid phase. For example, if cyclohexanol is employed as the solvent, one can expect a temperature rise ($\Delta T$) of nearly four times that obtained as when, for example, methanol is the solvent. Such an increase in temperature adversely affects product selectivity in that conditions favoring cracking reactions are encountered. Likewise, the processing pressures and solvents set forth herein enable the reaction to be conducted under conditions which are not favorable to the formation of secondary and tertiary amines. In addition, and in combination with the solvent described above, the presence of ammonia functions to deter the formation of secondary and tertiary amines. The combination of processing conditions, solvent and ammonia result in the formation of alkyl-1,3-aminopropanes with minimal amounts of secondary and tertiary amine by-products and minimal amounts of by-product primary amines otherwise formed from cleavage of the starting nitrile.

The process described herein can be operated batchwise or in a continuous manner by passing the liquid nitrile over or through a catalyst bed. A continuous stirred tank reactor can also be utilized where the reactant solution of nitrile and solvent is injected into the reactor at a temperature lower than that prevailing in the reactor. Alternatively, the continuous process can be conducted in a manner such that the nitrile and solvent in the presence of hydrogen and ammonia are passed through a bed of hydrogenation catalyst at a weight hourly space velocity (WHSV) of from about 0.05 to 5 weight percent of nitrile per hour per weight of catalyst and preferably at a WHSV of about 0.10 to 2.

Alkyl-1,3-diaminopropanes prepared according to this invention include N-[n-decyl]-1,3-diaminopropane, N-[sec-decyl]-1,3-diaminopropane, N-[n-decyl]-1,3-diamino-2-methylpropane, N-[n-undecyl]-1,3-diaminopropane, N-[secundecyl]-1,3-diaminopropane, n-[n-dodecyl]-1,3-diaminopropane, N-[n-dodecyl]-1,3-diamino-2-methylpropane, N-[n-tridecyl]-1,3-diaminopropane, N-[sec-tridecyl]-1,3-diaminopropane, N-[n-hexadecyl]-1,3-diaminopropane, N-[n-eicosyl]-1,3-diaminopropane, N-[n-tetracosyl]-1,3-diaminopropane, N-[n-tetracosyl]-1,3-diamino-2-methylpropane, N-[sec-tetracosyl]-1,3-diaminopropane; mixtures of N-[n-($C_{10-14}$)alkyl]-1,3-diaminopropanes; mixtures of N-[sec-($C_{10-14}$)alkyl]-1,3-diaminopropanes; mixtures of N-[n-tetradecyl]-1,3-diaminopropane, N-[n-pentadecyl]-1,3-diaminopropane and N-[n-hexadecyl]-1,3-diaminopropane; mixtures of N-[sec-($C_{14-16}$)alkyl]-1,3-diaminopropanes; and mixtures of N-[sec-($C_{18-24}$)alkyl]-1,3-diaminopropanes. The alkyl-1,3-diaminopropanes prepared herein are useful as corrosion inhibitors, for example when complexed with zinc mercaptobenzothiazole, as additives for lubricants and fuels and as surfactants. In addition, they can be employed as raw materials for synthetic detergents, waxes, germicides and waterproofing agents.

In order to more fully illustrate the nature of our invention and the manner of practicing the same, the following examples are presented.

EXAMPLE

A tubular reactor four feet in length was packed with 5.78 pounds of commercially available hydrogenation catalyst composed of nickel on kieselguhr promoted with zirconium. The catalyst was treated under reducing conditions of 500° F. at 600 p.s.i.g. for three hours with hydrogen flowing at 6 standard cubic feet per hour downflow. After the activation, the reactor was cooled to 220° F. and the charge stock, hydrogen and ammonia were concurrently passed downflow. The charged material consisted of 16.3 weight percent of a mixture of 2-[secondary($C_{10-14}$)alkyl primary amino] propionitriles, 2.4 weight percent ($C_{10}$–$C_{14}$) secondary alkyl primary amines and the remaining 81.3 weight percent being methanol. Approximately 30:1 mole ratio of hydrogen to ($C_{10}C_{14}$ secondary alkyl) aminopropionitriles and 20:1 mole ratio of ammonia to nitrile was used. The reaction was conducted under the following conditions: a reactor pressure 600 p.s.i.g., a reactor inlet temperature 219° F., a charge rate 0.825 pounds per hour of liquid feed, an ammonia rate of 115 grams per hour, and a hydrogen rate 8.1 standard cubic feet per hour. In the course of the reaction, the maximum temperature in the reactor was about 239° F. representing a rise of about 20° F. ($\Delta T$). The reaction product was vacuumed distilled and a mixture of N-[sec($C_{10-14}$)alkyl]-1,3-diaminopropanes was recovered in a 90 weight percent yield with a 96 percent conversion based on the nitrile charge. The temperature rise reported above is in contrast to an expected temperature rise on the order of 75° F. where a non-vaporizing solvent is used in place of methanol, such as cyclohexanol, under the adiabatic conditions as outlined above. In such an instance, the desired recoverable product would be reduced to the order of 60 to 70 weight percent.

We claim:

1. A catalytic hydrogenation process for preparing $C_{10}$ to $C_{30}$ alkyl-1,3-diaminopropanes which comprises contacting a $C_{10}$ to $C_{30}$ alkyl aminopropionitrile or mixtures thereof and an organic solvent having a normal boiling point of about 85 to 175° F. in the liquid phase with hydrogen and ammonia, wherein the volume ratio of gaseous hydrogen and ammonia to liquid nitrile and solvent is about 10:1 to about 100:1, in the presence of a hydrogenation catalyst at a reaction temperature of between about 180° F. and 260° F. and a pressure of between about 200 and 1000 p.s.i.g.

wherein said contacting is conducted non-isothermally at an increasing reaction temperature with progressive vaporization of said solvent and under sufficient pressure to prevent complete vaporization of said solvent, where the increase in reaction temperature is between 5 and 40° F.

2. A process according to claim 1 wherein said reaction temperature is between about 200 and 240° F.

3. A process according to claim 1 wherein said solvent has a normal boiling point of 85 to 150° F.

4. A process according to claim 1 wherein the weight ratio of said solvent to nitrile is about 2:1 to about 20:1.

5. A process according to claim 1 wherein the mole ratio of hydrogen to nitrile is about 16:1 to about 150:1.

6. A process according to claim 1 wherein the mole ratio of ammonia to nitrile is about 4:1 to about 50:1.

7. A process according to claim 1 wherein said solvent is methanol.

8. A process according to claim 1 wherein said solvent is ethylpropylether.

9. A process according to claim 1 wherein said solvent is methylacetate.

10. A process according to claim 1 wherein said solvent is ethylformate.

11. A process according to claim 1 wherein said solvent is propylamine.

12. A process according to claim 1 wherein said nitrile is a mixture of 2-[secondary ($C_{10-14}$) alkyl primary amino] propionitriles.

13. A process according to claim 1 wherein said catalyst is nickel on kieselguhr promoted with zirconium.

14. A process according to claim 1 wherein said catalyst is palladium on carbon.

* * * * *